United States Patent
Yuan

(10) Patent No.: US 7,022,494 B2
(45) Date of Patent: Apr. 4, 2006

(54) DETECTION OF POTASSIUM IONS USING ION-SENSITIVE ENZYMES

(75) Inventor: Chong-Sheng Yuan, San Diego, CA (US)

(73) Assignee: General Atomics, San Diego, CA (US)

( * ) Notice: Subject to any disclaimer, the term of this patent is extended or adjusted under 35 U.S.C. 154(b) by 148 days.

(21) Appl. No.: 10/665,888

(22) Filed: Sep. 19, 2003

(65) Prior Publication Data

US 2005/0069970 A1 Mar. 31, 2005

(51) Int. Cl.
*C12Q 1/58* (2006.01)

(52) U.S. Cl. ............................. 435/12; 435/4
(58) Field of Classification Search .................. 435/12, 435/4, 25, 26
See application file for complete search history.

(56) References Cited

U.S. PATENT DOCUMENTS

| | | | |
|---|---|---|---|
| 4,608,335 A | * 8/1986 | Fossati | 435/12 |
| 5,334,507 A | 8/1994 | Soya et al. | 435/25 |
| 5,501,958 A | 3/1996 | Berry et al. | 435/18 |
| 5,719,036 A | 2/1998 | Tadano et al. | 435/26 |

FOREIGN PATENT DOCUMENTS

JP 6-311897 * 11/1994

OTHER PUBLICATIONS

Kimura, S. et al. New Enzymatic Assay With Urea Amidolyase For Determining Potassium in Serum. Annals of Clinical Biochemistry 1997 vol. 34, pp. 384–388.*

Kimura S. New Enzymatic Assay with Urea Amidolyase for Determining Potassium in Serum. Ann Clin biochem 1997 34:384–388.*

Bergmeyer et al., Methods of Enzymatic Analysis (Bergmeyer H.U. ed) $2^{nd}$ V.1, 505–507, Academic Press, Inc., New York NY (1974).

Bettochi et al., Biosens. Bioelectron 11:1–10 (1996).

Biochemistry 11:1726 (1972).

Bonucchi et al., Int. J. Artif. Organs 10:352–56 (1987).

Inouye et al., J. Biochem. 131:97–105 (2002).

Kimura et al., Ann. Clin. Biochem. 34:384–388 (1997).

Lespinas et al., Clin. Chem. 35(4):654–58 (1989).

Näslund et al., Clin. Chem. 44(9):1964–73 (1998).

Roon et al., J. Biol. Chem. 247(13):4107–13 (1972).

Roon et al., Methods Enzymol. 17A:317–24 (1970).

Sumrada et al., J. Biol. Chem. 257(15):9119–27 (1982).

Tabata et al., J. Biolumin. Chemilumin. 2:63–67 (1988).

Tietz, Textbook of Clinical Chemistry, p. 1841, W.B. Saunders Co., Philadelphia (1986).

Watson et al., Molecular Biology of the Gene, $4^{th}$ Ed., The Benjamin/Cummings Pub. Co., p. 224 (1987).

* cited by examiner

*Primary Examiner*—Ralph Gitomer
(74) *Attorney, Agent, or Firm*—Morrison & Foerster LLP

(57) ABSTRACT

The invention relates generally to the field of potassium ion detection. In particular, the invention provides methods and kits for assaying for potassium ions in a sample, using, a potassium-dependent urea amidolyase (UAL).

19 Claims, 1 Drawing Sheet

DETECTION OF POTASSIUM IONS USING ION-SENSITIVE ENZYMES

BACKGROUND OF THE INVENTION

Serum electrolytes play a critical role in regulating normal physiologic functioning within and between cells. The testing of serum electrolytes is one of the most common analytical tests performed within hospitals. Such measurements are employed for routine monitoring of a patient as well as in emergency and life-threatening situations. Because of the vital role of electrolytes in normal physiologic responses, it is important that the measurement of the serum levels of electrolytes can be performed efficiently, accurately, and inexpensively.

Potassium is one electrolyte important in the regulation of intracellular enzymatic function and in proper electrical functioning of excitable tissues, e.g., the heart, brain, and muscle. Serum potassium is normally maintained within the narrow range of 3.5 to 5.5 mEq/l. The intracellular/extracellular potassium ratio ($K_i/K_e$) largely determines neuromuscular tissue excitability. Because most of the potassium ions are intracellular, neuromuscular excitability is markedly affected by small changes in extracellular, e.g., serum, potassium levels. For example, even small changes in potassium serum levels can cause abnormal cardiac arrhythmias, affecting cardiac function. Therefore, the monitoring of potassium serum levels provides useful information on a variety of diseases and disorders, including nephropathy (e.g., acute renal failure, chronic renal failure), endocrinopathy (e.g., primary and secondary aldosteronism), and cardiopathy.

Currently, the most commonly used methods to detect serum potassium are ion-selective electrode (ISE) and flame photometry. ISE relies on ion-specific electrodes. Ideally, each electrode possesses a unique ion-selective property that allows it to respond to the desired ion. However, in practice, interference from other ions in the sample compromise the specificity of the detecting electrode, rendering the electrodes susceptible to false readings. Moreover, the instrumentation for ISE is relatively expensive, requires routine maintenance that is sometimes cumbersome and time-consuming, and demands that the operating technician have a considerable degree of skill and knowledge to achieve accurate and consistent readings. Flame photometry relies on the principle that certain atoms, when energized by heat, become excited and emit a light of characteristic wavelength of radiant energy when returning to ground state. The intensity of the characteristic wavelength of radiant energy produced by atoms in the flame is directly proportional to the number of atoms excited in the flames, which is directly proportional to the concentration of the substance of interest in the sample. Like ISE, the instrumentation required for this method is complex and relatively expensive. Moreover, flame photometry requires the use of combustible gas, introducing sometimes expensive hazard prevention measures. Thus, conventional methods to detect potassium ions in samples are limited by complex instrumentation, potentially expensive and cumbersome maintenance, additional hazards, and often time requirements not suitable to emergency situations.

Potassium detection can also be achieved by enzymatic detection. Pyruvate kinase (U.S. Pat. Nos. 5,501,958 and 5,334,507) and glycerol dehydrogenase (U.S. Pat. No. 5,719,036) are described in enzymatic potassium detection methods. However, for each of these enzymes, interference from other ions constitutes a major limitation on the accuracy and usefulness of the assay. For example, the inference from $NH_3$ ions requires additional steps with anti-interference agents to render the enzymatic method accurate.

The present invention addresses the problems with the conventional and enzymatic detection systems discussed above and provides an efficient, inexpensive, and accurate method in a format that is more user friendly in automated analyzers.

BRIEF SUMMARY OF THE INVENTION

In one aspect, the present invention is directed to a method for assaying for potassium ions in a sample, which method comprises: a) contacting the sample with a potassium dependent urea amidolyase (UAL), wherein the UAL consumes urea and forms $P_i$; and b) assessing the consumption of urea or the formation of $P_i$ in step a) to determine the presence or amount of potassium ions in the sample.

In another aspect, the present invention is directed to a method for assaying for potassium ions in a sample, which method comprises: a) contacting the sample with a first composition comprising a potassium-dependent urea amidolyase; b) contacting the sample with a second composition comprising urea; and c) assessing the production of $P_i$ to determine the presence or amount of potassium ions in the sample. In one embodiment, the first composition further comprises glycogen, phosphorylase a, oxidized β-nictinamide adenine dinucleotide (NAD), phosphoglucomutase, glucose-6-phosphate dehydrogenase (G-6-PDH), 2-(4-iodophenyl)-3-(4-nitrophenyl)-5(2,4-disulfophenyl)-2H-tetrazolium (WST-1), and 1-methoxy-5-methyl-phenazinium methyl sulfate (PMS), and the second composition further comprises adenine triphosphate (ATP), a protein, $MgCl_2$, and a buffer. Kits for assaying for potassium ions using the method are also provided.

DETAILED DESCRIPTION OF THE INVENTION

Figure 1:
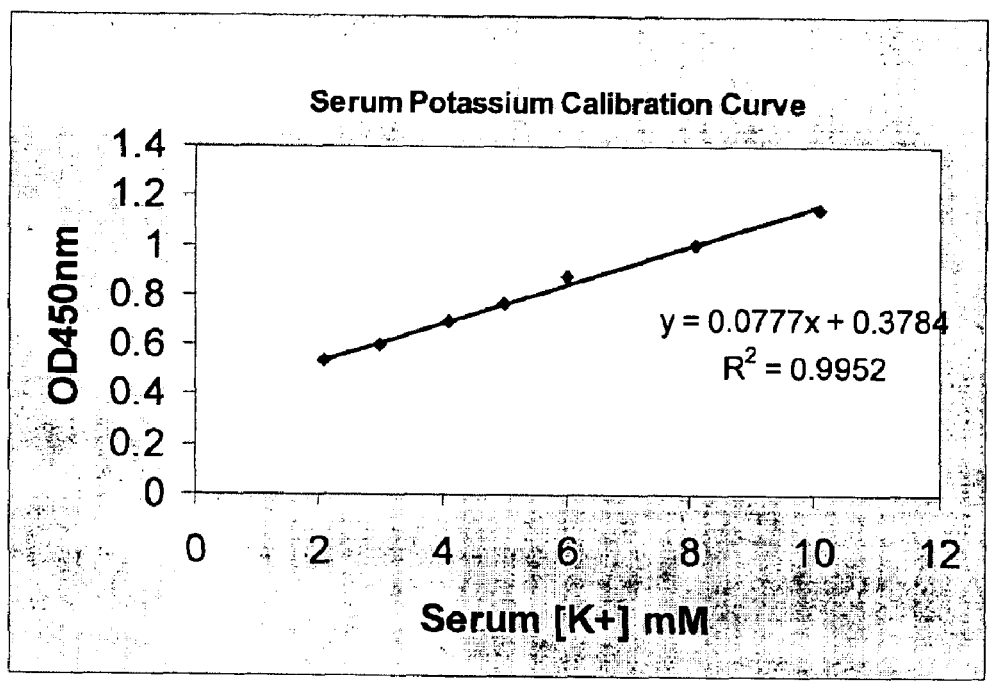
FIG. 1 is a potassium calibration curve. The calibration curve was generated using the methods disclosed in the Example 1. Briefly, the calibration curve was constructed by plottin the ΔA values of the standards against the corresponding potassium concentration.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "urea amidolyase" refers to an enzyme catalyzing the carboxylation of urea to yield corresponding ADP, $HCO_3^-$, $OH^-$ and $P_i$, as shown in the following reactions:

Reaction A:

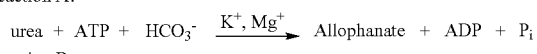
urea + ATP + $HCO_3^-$ $\xrightarrow{K^+, Mg^+}$ Allophanate + ADP + $P_i$ Reaction B:

Allophanate $\longrightarrow$ $2NH_3$ + $2CO_2$, resulting in the net reaction of:

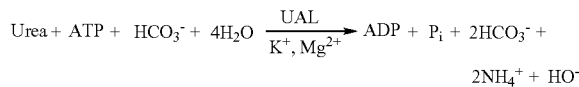
Urea + ATP + $HCO_3^-$ + $4H_2O$ $\xrightarrow[K^+, Mg^{2+}]{UAL}$ ADP + $P_i$ + $2HCO_3^-$ +

$2NH_4^+$ + $HO^-$

Other synonyms of urea amidolyase include urease (ATP-hydrolysing); urea carboxylase (hydrolysing); ATP-urea amidolyase; urea carboxylase; urea amido-lyase; UALase, and urea:carbon-dioxide ligase. For purposes herein, the name "urea amidolyase" is used herein, although all such chemical synonyms are contemplated. "Urea amidolyase" also encompasses a functional fragment or a derivative that still substantially retain its enzymatic activity catalyzing the carboxylation of urea to yield corresponding ADP and $P_i$. Typically, a functional fragment or derivative retains at least 50% of its urea amidolyase activity. Preferably, a functional fragment or derivative retains at least 60%, 70%, 80%, 90%, 95%, 99% or 100% of its urea amidolyase activity. It is also intended that a urea amidolyase can include conservative amino acid substitutions that do not substantially alter its activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., *Molecular Biology of the Gene*, 4th Edition, 1987, The Benjamin/Cummings Pub. Co., p. 224). Such exemplary substitutions are preferably made in accordance with those set forth in TABLE 1 as follows:

TABLE 1

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions.

As used herein, a "composition" refers to any mixture of two or more products or compounds. It may be a solution, a suspension, liquid, powder, a paste, aqueous, non-aqueous, or any combination thereof.

As used herein, a "combination" refers to any association between two or among more items.

As used herein, "biological sample" refers to any sample from a biologic source, including but not limited to blood, plasma, and serum samples.

As used herein, "plasma" refers to the fluid, noncellular portion of the blood, distinguished from the serum obtained after coagulation.

As used herein, "serum" refers to the fluid portion of the blood obtained after removal of the fibrin clot and blood cells, distinguished from the plasma in circulating blood.

As used herein, "whole blood sample" refers to the fluid and cellular portion of the plasma in circulating blood.

As used herein, "red blood cell sample" refers to the cellular portion of the blood obtained after removal of the serum portion from the plasma in circulating blood.

As used herein, "fluid" refers to any composition that can flow. Fluids thus encompass compositions that are in the form of semi-solids, pastes, solutions, aqueous mixtures, gels, lotions, creams, and other such compositions.

As used herein, "phosphorylase a" refers to an enzyme that catalyzes the phosphorylation of glycogen to form $\alpha$-D-glucose-1-$P_i$. It is intended to encompass a phosphorylase a with conservative amino acid substitutions that do not substantially alter its desired activity.

As used herein, "phosphoglucomutase" refers to an enzyme that catalyzes the phosphorylation of $\alpha$-D-glucose-1-$P_i$ to form $\alpha$-D-glucose-6-$P_i$. Synonyms for the enzyme include glucose phosphomutase and phosphoglucose mutase. It is intended to encompass a phosphoglucomutase with conservative amino acid substitutions that do not substantially alter its desired activity.

As used herein, "glucose-6-phosphate dehydrogenase" refers to an enzyme that catalyzes the formation of NADH and 6-phosphogluconate by consuming $\alpha$-D-glucose-6-$P_i$ and NAD. It is intended to encompass a glucose-6-phosphate dehydrogenase with conservative amino acid substitutions that do not substantially alter its desired activity.

As used herein, "peroxidase" refers to an enzyme that catalyzes a host of reactions in which hydrogen peroxide is a specific oxidizing agent and a wide range of substrates act as electron donors. It is intended to encompass a peroxidase with conservative amino acid substitutions that do not substantially alter its activity. The chief commercially available peroxidase is horseradish peroxidase.

As used herein, the abbreviations for any protective groups, amino acids and other compounds are in accord with their common usage, recognized abbreviations, or the IUPAC-IUB Commission on Biochemical Nomenclature, unless otherwise indicated (see *Biochemistry* 11: 1726 (1972)).

B. Methods and Kits for Assaying for Potassium Ions Using Urea Amidolyase

In one aspect, the present invention is directed to a method for assaying for potassium ions in a sample, which method comprises: a) contacting the sample with a potassium dependent urea amidolyase (UAL), wherein the UAL consumes urea and forms $P_i$; and b) assessing the consumption of urea or the formation of $P_i$ in step a) to determine the presence or amount of potassium ions in the sample.

In another aspect, the present invention is directed to a method for assaying for potassium ions in a sample, which method comprises: a) contacting the sample with a first composition comprising a potassium-dependent urea amidolyase; b) contacting the sample with a second composition comprising urea; and c) assessing the production of $P_i$ to determine the presence or amount of potassium ions in the sample. In one embodiment, the first composition further comprises glycogen, phosphorylase a, oxidized β-nictinamide adenine dinucleotide (NAD), phosphoglucomutase, glucose-6-phosphate dehydrogenase (G-6-PDH), 2-(4-iodophenyl)-3-(4-nitrophenyl)-5(2,4-disulfophenyl)-2H-tetrazolium (WST-1), and 1-methoxy-5-methyl-phenazinium methyl sulfate (PMS), and the second composition further comprises adenine triphosphate (ATP), a protein, $MgCl_2$, and a buffer.

Any suitable potassium-dependent urea amidolyase can be used. It is not limited to any particular source. In one embodiment, the urea amidolyase is of yeast origin. See, e.g., Roon et al., Methods Enzymol. 17A: 317–24 (1970); Roon et al., J. Biol. Chem. 247:4107–13 (1972); and Sumrada et al., J. Biol. Chem. 257:9119–27 (1982). A functional fragment or a derivative of urea amidolyase that still substantially retains its enzymatic activity catalyzing the formation of ADP, $P_i$, $HCO_3^-$, and $OH^-$ from urea and ATP can also be used.

Normally, a functional fragment or a derivative of a urea amidolyase retains at least 50% of its enzymatic activity. Preferably, a functional fragment or a derivative of a urea amidolyase retain at least 50%, 60%, 70%, 80%, 90%, 95%, 99% or 100% of its enzymatic activity.

The enzymatic activity of urea amidolyase can be assessed by any suitable methods. Exemplary methods of assessing urea amidolyase activity include that of Näslund et al., Clin. Chem. 44(9):1964–73 (1998); Lespinas et al., Clin. Chem. 35:654–58 (1989); Bonucchi et al., Int. J. Artif Organs 10:352–56 (1987); Bettocchi et al., Biosens. Bioelectron 11:1–10 (1996); and Tabata et al., J. Biolumin. Chemilumin. 2:63–67 (1988). For example, the enzymatic activity of the urea amidolyase in the presence of potassium can be assessed by assessing consumption of the ATP or urea in the reaction or the formation of ADP and $P_i$.

In one embodiment, the formation of $P_i$ can be assessed using a combination of phosphorylase a, phosphoglucomutase, and glucose-6-phosphate dehydrogenase (G-6-PDH). For example, the following series of coupled enzymatic reactions can result in the production of NADH, which can be used to reduce a reagent into a detectable product:

Reaction (I):

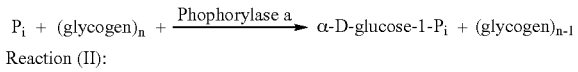

Reaction (II):

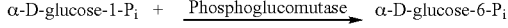

Reaction (III):

Reaction (IV):

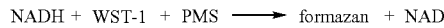

Any suitable phosphorylase a, phosphoglucomutase, and G-6-PDH can be used. The enzymes can be derived, isolated, or recombinantly produced from any source known in the art, including yeast, microbial, and mammalian, that will permit the generation of a suitable product that can generate a detectable reagent.

The chromagen of the reduced type to be used herein is not particularly limited. In one embodiment, the chromagen is a water soluble colorless tetrazolium salt. Examples of chromagens that once reduced produce a detectable reagent include 2-(4-iodophenyl)-3-(4-nitrophenyl)-5(2,4-disulfophenyl)-2H-tetrazolium (WST-1), 2-(4-Iodophenyl)-3-(2,4-dinitrophenyl)-5-(2,4-disulfophenyl)-2H-tetrazolium (WST-3), 2-Benzothiazolyl-3-(4-carboxy-2-methoxyphenyl)-5-[4-(2-sulfoethylcarbamoyl)phenyl]-2H-tetrazolium salt] (WST-4), and 2,2'-Dibenzothiazolyl-5,5'-bis[4-di(2-sulfoethyl)carbamoylphenyl]-3,3'-(3,3'-dimethoxy-4,4'-biphenylene)ditetrazolium (WST-5). In one preferred embodiment, the tetrazolium salt is 2-(4-iodophenyl)-3-(4-nitrophenyl)-5(2,4-disulfophenyl)-2H-tetrazolium (WST-1). WST-1 is the basic model in the WST series. WST-1 is readily reduced by NADH to the colored formazan in the presence of an electron mediator such as 1-methoxy PMS. The amount of the resulting formazan is directly proportional to the concentrations of NADH. The detection sensitivity for NADH using WST-1 (at 438 nm) is approximately 1.7 times greater than that using Nitro TB. The absorption maximum (1max) of WST-1 formazan is 438 nm (molar absorption coefficient=$3.7 \times 10^4$, pH 4–9).

The sample can be contacted with the urea amidolyase and the urea sequentially or simultaneously. Likewise, any suitable means for assessing enzymatic activity in the presence of potassium can be contacted with the urea amidolyase sequentially or simultaneously in a fashion that permits the formation of a detectable product. In one embodiment, the presence or amount of potassium ions is measured by contacting a sample with the reagents containing urea amidolyase, glycogen, phosphorylase a, phosphoglucomutase, G-6-PDH, NAD, urea, Mg2+, and ATP to form NADH which is utilized under the coexistence of a chromagen, e.g., WST-1, and an electron mediator, e.g., PMS, to produce a detectable dye, e.g., formazan. The sample is then analyzed by standard colorimetric analysis.

Any suitable conditions for detection or measurement of potassium ions can be used. The reaction temperature is usually in the range from 10° C. to 40° C., with a preferred temperature of 37° C. The reaction time is preferably not more than 30 minutes, most preferably about 15 minutes or less.

Any suitable means of performing colorimetric analysis can be used. In one embodiment, the samples are analyzed for the presence of formazan in a Roche Cobas Mira Chemical Analyzer.

If desirable, interference of the assay can be countered. For example, ascorbate interference can be countered using a copper (II) compound, a cholic acid or a bathophenanthroline disulphonic acid or a mixture thereof. Bilirubin interference can be countered using a ferrocyanide salt.

The present methods can be used to assay any suitable sample. Preferably, the sample is a biological sample. In one example, the sample is a blood sample, e.g., a plasma, serum, red blood cell or whole blood sample.

Any suitable means for preparing the sample may be employed. In one embodiment, serum or plasma samples are treated with EDTA-Na or heparinate.

The present methods can be used for any suitable purpose. Preferably, the method is used in prognosis or diagnosis of a disease or a disorder. In particular, the methods are useful in detecting the presence of or quantitating the amount of potassium ions in a sample, preferably a biological sample, more preferably a serum or plasma sample.

In yet another aspect, the present invention is directed to a kit for assaying for potassium ion concentration in a biological sample, which kit comprises: a) a first composition comprising a potassium-dependent urea amidolyase, wherein the amidolyase forms consumes urea and produces $P_i$; and b) means for assessing the urea consumed or the $P_i$ formed by the amidolyase to determine the presence or amount of the potassium ions in the sample. In one embodiment, the first composition further comprises glycogen, phosphorylase a, oxidized β-nictinamide adenine dinucleotide (NAD), phosphoglucomutase, glucose-6-phosphate dehydrogenase (G-6-PDH), 2-(4-iodophenyl)-3-(4-nitrophenyl)-5(2,4-disulfophenyl)-2H-tetrazolium (WST-1), and 1-methoxy-5-methyl-phenazinium methyl sulfate (PMS), wherein the reduction of WST-1 in the presence PMS to form formazan is the means for assessing the product formed if potassium ions are present. In one embodiment, the kit further comprising a second composition comprising urea, adenine triphosphate (ATP), $MgCl_2$. In a specific embodiment, the second compositions can further comprise a protein, e.g., bovine serum albumin, and a buffer, $NaHCO_3$.

Any suitable means for assessing the urea consumed or the $P_i$ formed by the amidolyase can be included in the present kits. For example, the means for assessing the formation of $P_i$ by urea amidolyase can comprise a series of reagents that include glycogen, phosphorylase a, oxidized β-nictinamide adenine dinucleotide (NAD), phosphoglucomutase, glucose-6-phosphate dehydrogenase (G-6-PDH), 2-(4-iodophenyl)-3-(4-nitrophenyl)-5(2,4-disulfophenyl)-2H-tetrazolium (WST-1), and 1-methoxy-5-methyl-phenazinium methyl sulfate (PMS), urea, adenine triphosphate (ATP), and $MgCl_2$, whose combination results in the production of formazan in levels that correlate with the presence of potassium in the sample.

The urea, glycogen, and adenosine triphosphate (ATP) to be used herein may be in the form of a salt which is not particularly limited, so long as it contains no potassium ions. A preferred form of glycogen is from oyster type II. A preferred form of ATP is adenosine triphosphate disodium salt.

The compositions of the present invention may be formulated into a reagent having a pH adjusted by the addition of a buffer to pH 6 to 9. Any suitable buffer may be used. It is contemplated that such buffers contain no potassium ions. Exemplary buffers are Good's buffer, triethanolamine buffer, and tris buffer.

The compositions of the present invention may further contain any surfactant, preservative, stabilizer, and enzyme activator. Preferred examples of the surfactant are Triton-100. Preferred examples of the preservative include $NaN_3$. Any suitable stabilizer can be used. In one embodiment, the stabilizer is a protein. In a specific embodiment, the protein is bovine serum albumin. Any suitable enzyme activator can be used. In one embodiment, the activator is $Mg^{2+}$ or a salt thereof, e.g., $MgCl_2$.

Any suitable concentration of urea amidolyase can be used in a composition for measurement of potassium ions. In a preferred embodiment, the concentration is in the range of 0.1–2 u/ml, more preferably, 0.3–1 u/ml, most preferably 0.4–0.6 u/ml. Any suitable concentration of phosphorylase a can be used. In a preferred embodiment, the concentration is in the range of 0.1–10 u/ml, more preferably, 1–5 u/ml, most preferably 2–3 u/ml. Any suitable concentration of phosphoglucomutase can be used. In a preferred embodiment, the concentration is in the range of 0.1–10 u/ml, more preferably, 1–5 u/ml, most preferably 2–3 u/ml. Any suitable concentration of G-6-PDH can be used. In a preferred embodiment, the concentration is in the range of 0.1–10 u/ml, more preferably, 1–5 u/ml, most preferably 2–3 u/ml.

The chromagen of the reduced type, adenosine triphosphate or a salt thereof, glycogen or a salt thereof, and 1-methoxy-5-methyl-phenazinium methyl sulfate (PMS) or a salt thereof are used at any concentration suitable for measurement. The chromagen of the reduced type is preferably used at a concentration in the range of 0.01 to 10 mM. The adenosine triphosphate or salt thereof is preferably used at a concentration of 1 to 20 mM. The glycogen or salt thereof is preferably used at a concentration of 0.1–1%. PMS or salt thereof is preferably used at a concentration of 0.05–0.5 mM.

In some embodiments, standards for calibration of the assay are included. In one embodiment, a low potassium serum standard and a high potassium standard are included. Preferably, the low potassium serum standard comprises 2.0–3.5 mM of potassium, preferably 3.0 mM, in serum and the high potassium serum standard comprises 7–10 mM of potassium, preferably 7.0 mM, in serum. In one embodiment, the presence or amount of potassium ions are calculated using a calibration curve. The amount of detectable chromagen is assessed at time 1 for a value of $A_1$ and at time 2 for a value of $A_2$. The resultant value is calculate in the following equation: $\Delta A = A_2 - A_1$. A calibration curve is generated by plotting the $\Delta A$ values of the standards. The amount of potassium in the samples are then determined by plotting the sample $\Delta A$ value on the calibration curve. In one embodiment, time 1 is 2 minutes after the addition of means to assess $P_i$ production and time 2 is 7–8 minutes after time 1.

C. EXAMPLES

Example 1

Potassium Ion Detection Assay Kit

Intended Use. The exemplary assay kit was for the quantitative in vitro determination of potassium in serum and plasma.

Assay Principle. Potassium was determined spectrophotometrically through a kinetic coupling assay system using potassium dependent urea amidolyase (UAL) as shown in Table 1. NADH generated in a coupling enzymatic reaction reduced the water soluble colorless tetrazolium salt, WST-1, in the presence of an electron mediator, 1-methoxy-5-methyl-phenazinium methyl sulfate (PMS), to form a water soluble formazan dye (maximum absorbance at 438 nm). The corresponding increase of optical density at 438 nm was proportional to the potassium concentration in the serum, as determined in a Roche Cobas Mira Chemical Analyzer.

TABLE 1

$$\text{Urea} + \text{ATP} + \text{HCO}_3^- + 4\text{H}_2\text{O} \xrightarrow[\text{K}^+, \text{Mg}^{2+}]{\text{UAL}} \text{ADP} + \text{Pi} + 2\text{HCO}_3^- + 2\text{NH}_4^+ + \text{OH}^-$$

$$P_i + (\text{Glycogen})_n \xrightarrow{\text{Phosporylase a}} \alpha\text{-D-Glucose-1-}P_i + (\text{Glycogen})_{n-1}$$

TABLE 1-continued

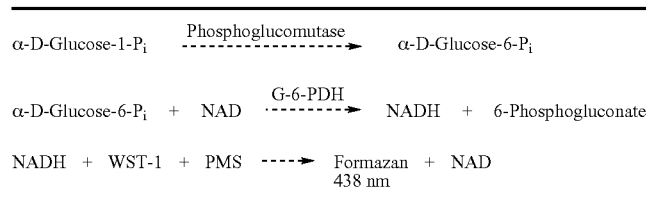

UAL: Urea Amidolyase
G-6-PDH: Glucose-6-phosphate Dehydrogenase
NAD: β-Nicotinamide Adenine Dinucleotide oxidized form
NADH: β-Nicotinamide Adenine Dinucleotide reduced form
WST-1: 2-(4-Iodophenyl)-3-(4-nitrophenyl)-5(2,4-disulfophenyl)-2H-tetrazolium
PMS: 1-methoxy-5-methyl-phenazinium methyl sulfate Key Assay Characteristics. The potassium enzymatic assay was a two reagent (R1 and R2) based kinetic assay system. The results were obtained in 15 min by measuring absorbance at 450 nm. No off line pretreatment was needed. The assay had a wide measuring range from 2 to 8 mmol/L. The assay offers excellent precision as shown in Table 2 below:

TABLE 2

|  | 4.1 mM K$^+$ | 6.1 mM K$^+$ |
| --- | --- | --- |
| Intra-assay | Mean = 4.1, CV % = 3.7% | Mean = 6.1 mM CV % = 2% |
|  | 4.4 mM K$^+$ | 6.4 mM K$^+$ |
| Inter-assay | Mean = 4.4 CV % = 3.2% | Mean = 6.5 CV % = 4.0% |

Reagent Preparation. One vial of Reagent 1 (R1) was reconstituted with 50 ml distilled water. The reagent was mixed gently by inversion and then allowed to stand for a minimum of 10 min at room temperature before use. The reconstituted R1 solution was stable for 1 week at 2–8° C. One vial of Reagent 2 (R2) was reconstituted with 25 ml of distilled water. The reagent was mixed gently by inversion and then allowed to stand for a minimum of 10 min at room temperature before use. The reconstituted R2 solution was stable for 1 week at 2–8° C.

TABLE 3

| Reagents |
| --- |
| Reagent 1 Buffer/enzyme/substrates |
| Lyophilized powder containing Enzyme/substrates, WST-1, PMS and stabilizers |
| Reagent 2 Buffer/protein/substrate |
| Lyophilized powder containing Protein/substrate and stabilizers |
| Low potassium Serum Standard  3.0 mM |
| High potassium Serum Standard  7.0 mM |

Low and High Serum Standards. Low and high serum K$^+$ standards were included and ready to use. The standards were stable up to expiration date when stored under 2–8° C.

Normal K$^+$ values in serum. The normal values were 3.5–5.1 mM (13.7–19.9 mg/dL).

Calibration and Quality Control. This assay was calibrated daily using the low and high potassium standards. A calibration curve was constructed by plotting the ΔA values of the standards against the corresponding potassium concentrations. The potassium concentration of the sample was determined by using the calibration curve.

Sample Specimens. The tested samples were serum or plasma treated with EDTA-Na or heparinate.

Assay Procedures.

1. R1 and R2 reagents were reconstituted as described in Reagent Preparation section and kept on an ice bath.
2. In a cuvette, 180 μL of Reagent R1 and 10 μL of serum sample were mixed and incubated at 37° C. for 5 minutes, and then 85 μL of Reagent 2 was added.
3. Absorbance (450 nm) was read at 2 minutes after addition of Reagent 2 as $A_1$. The sample was incubated for 8 more minutes, and the absorbance was read again as $A_2$.
4. Calculate $\Delta A = A_2 - A_1$

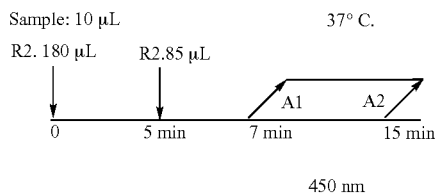

Interference. The assay was not interfered by the following substances at indicated concentrations: Na$^+$ 200 mM, NH$_4^+$ 0.5 mM, Ca$^{2+}$ 5.0 mM, Mg$^{2+}$ 5.0 mM, ascorbic acid 5.0 mM, and bilirubin 10 mg/dl, 1.5 mM P$_i$, 0.25 mM CuCl$_2$, and 5 mM glucose.

References.
1. N. Tietz. *Textbook of Clinical Chemistry*, p. 1841. W. B. Sauders Company, Philadelphia (1986)
2. S. Kimura, S. Iyama, Y. Yamaguchi, S. Hayashi, R. Fushimimi and N. Amino. *Ann. Clin. Biochem* (1997), 34:384–388
3. K. Inouye, I. Ueno, S. Yokoyama, and T. Sakaki *J. Biochem.* 131, 97–105(2002)
4. H. Bergmeyer, K. Gawehn, and M. Grassl in *Methods of Enzymatic Analysis* (Bergmeyer H. U. ed) 2$^{nd}$ Volume I, 505–507, Academic Press, Inc. New York, N.Y. (1974)

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

What is claimed is:

1. A method for assaying for potassium ions in a sample, which method comprises:
    a) contacting the sample with a potassium dependent urea amidolyase (UAL), wherein the UAL catalyzes the carboxylation of urea and forms $P_i$ and ADP; and
    b) assessing the concentration of urea and/or the formation of $P_i$ in step a) to assay for the presence or amount of potassium ions in the sample.

2. The method of claim 1, wherein the sample is a biological sample.

3. The method of claim 2, wherein the biological sample is a blood sample.

4. The method of claim 3, wherein the blood sample is a plasma, serum, red blood cell, or whole blood sample.

5. The method of claim 1, wherein the UAL catalyzes the formation of $P_i$ in the following net reaction:

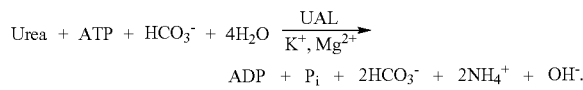

$$\text{Urea} + \text{ATP} + \text{HCO}_3^- + 4\text{H}_2\text{O} \xrightarrow[K^+, Mg^{2+}]{UAL} \text{ADP} + P_i + 2\text{HCO}_3^- + 2\text{NH}_4^+ + \text{OH}^-.$$

6. The method of claim 1, wherein the amount of $P_i$ formed correlates with the amount of potassium ions in the sample.

7. The method of claim 1, which is used in a prognosis or diagnosis of a disease or disorder.

8. A method for assaying for potassium ions in a sample, which method comprises:
    a) contacting the sample with a first composition comprising a potassium-dependent urea amidolyase;
    b) contacting the sample with a second composition comprising urea; and
    c) assessing the production of $P_i$ to determine the presence or amount of potassium ions in the sample.

9. The method of claim 8, wherein the sample is a biological sample.

10. The method of claim 9, wherein the biological sample is a blood sample.

11. The method of claim 10, wherein the blood sample is a plasma, serum, red blood cell, or whole blood sample.

12. The method of claim 8, wherein the first composition further comprises glycogen, phosphorylase a, oxidized β-nictinamide adenine dinucleotide (NAD), phosphoglucomutase, glucose-6-phosphate dehydrogenase (G-6-PDH), 2-(4-iodophenyl)-3-(4-nitrophenyl)-5(2,4-disulfophenyl)-2H-tetrazolium (WST-1), and 1-methoxy-5-methyl-phenazinium methyl sulfate (PMS), and the second composition further comprises adenine triphosphate (ATP) and $MgCl_2$.

13. The method of claim 12, wherein the second composition further comprises a protein.

14. The method of claim 13, wherein the protein is bovine serum albumin (BSA).

15. The method of claim 12, wherein the second composition further comprises a buffer.

16. The method of claim 15, wherein the buffer is $NaHCO_3$.

17. The method of claim 12, wherein the assessing of production of Pi comprises detecting a detectable product.

18. The method of claim 8, which is used in a prognosis or diagnosis of a disease or disorder.

19. The method of claim 17, wherein the detectable product is formazan.

* * * * *